United States Patent
Iustin et al.

(10) Patent No.: US 9,707,041 B2
(45) Date of Patent: Jul. 18, 2017

(54) MODEL BASED POSITIONING SYSTEM

(71) Applicant: MICROPOS MEDICAL AB, Göteborg (SE)

(72) Inventors: Roman Iustin, Mölndal (SE); Johan Linder, Göteborg (SE); Erik Isberg, Bjästa (SE); Tomas Gustafsson, Mölndal (SE); Bo Lennernäs, Uddevalla (SE)

(73) Assignee: Micropos Medical AB, Gothenburg (SE)

( * ) Notice: Subject to any disclaimer, the term of this patent is extended or adjusted under 35 U.S.C. 154(b) by 44 days.

(21) Appl. No.: 14/692,348

(22) Filed: Apr. 21, 2015

(65) Prior Publication Data

US 2015/0223904 A1    Aug. 13, 2015

Related U.S. Application Data

(62) Division of application No. 11/851,356, filed on Sep. 6, 2007, now Pat. No. 9,042,962.

(30) Foreign Application Priority Data

Dec. 22, 2006  (SE) ...................................... 0602822

(51) Int. Cl.
*A61B 5/05*    (2006.01)
*A61B 19/00*   (2006.01)
(Continued)

(52) U.S. Cl.
CPC ............ *A61B 19/5244* (2013.01); *A61B 5/06* (2013.01); *A61B 34/20* (2016.02); *A61N 5/1049* (2013.01); *H04B 17/21* (2015.01); *A61B 5/05* (2013.01); *A61B 5/062* (2013.01); *A61B 2034/2051* (2016.02); *A61B 2034/2065* (2016.02); *A61B 2560/0228* (2013.01);
(Continued)

(58) Field of Classification Search
USPC ....... 600/407, 409, 424, 431, 433, 434, 435; 702/94, 95; 128/899
See application file for complete search history.

(56) References Cited

U.S. PATENT DOCUMENTS 6,246,231 B1   6/2001  Ashe
6,345,114 B1   2/2002  Mackie et al.
(Continued)

FOREIGN PATENT DOCUMENTS

WO   WO 2005/104976 A1   11/2005
WO   WO 2006/091145 A1    8/2006

*Primary Examiner* — Tse Chen
*Assistant Examiner* — Jason Ip
(74) *Attorney, Agent, or Firm* — Birch, Stewart, Kolasch & Birch, LLP

(57) ABSTRACT

The present invention relates to a model based positioning system that includes a positioning device having at least one transmitter configured to be in a tracking environment, e.g. inserted into a body, a receiver having a plurality of receiver elements arranged outside the tracking environment, a control unit configured to measure amplitude and/or phase information of a signal transmitted from the at least one transmitter and received at each receiving element, and a memory unit for storing a model for each receiving element. The control unit is also configured to estimate the position P of the positioning device by comparing the model for each receiving element with the measured received signal for each receiving element.

15 Claims, 7 Drawing Sheets

(51) Int. Cl.
    *A61B 5/06* (2006.01)
    *A61N 5/10* (2006.01)
    *H04B 17/21* (2015.01)
    *A61B 34/20* (2016.01)
    *G01S 5/02* (2010.01)

(52) U.S. Cl.
    CPC ............... *A61B 2560/0238* (2013.01); *A61N 2005/1051* (2013.01); *G01S 5/021* (2013.01)

(56) References Cited

U.S. PATENT DOCUMENTS

| | | |
|---|---|---|
| 6,636,757 B1 | 10/2003 | Jascob et al. |
| 2002/0085668 A1 | 7/2002 | Blumhofer et al. |
| 2003/0216639 A1 | 11/2003 | Gilboa et al. |
| 2005/0003757 A1 | 1/2005 | Anderson |
| 2005/0015071 A1 | 1/2005 | Brimhall |
| 2005/0024043 A1 | 2/2005 | Govari |
| 2005/0046608 A1 | 3/2005 | Schantz et al. |
| 2006/0116571 A1 | 6/2006 | Maschke et al. |
| 2006/0187059 A1 | 8/2006 | Fabian et al. |

MODEL BASED POSITIONING SYSTEM

This application is a Divisional of copending application Ser. No. 11/851,356, filed on Sep. 6, 2007, which claims priority under 35 U.S.C. §119(a) to Application No. 0602822-9, filed in Sweden on Dec. 22, 2006, all of which are hereby expressly incorporated by reference into the present application.

TECHNICAL FIELD

The present invention relates to a model based positioning system, especially for a positioning system used in medical applications. The invention also relates to a method for calibrating the positioning system, and a method for tracking a positioning device within a body using the positioning system.

BACKGROUND

Several positioning systems exist today, that are used to determine a three-dimensional position of an implantable positioning device in a body. These positioning systems are particularly suited for tracking the position of a cancer area for radiation therapy (radiotherapy).

One type of system is based on radio frequency transmission from an implantable positioning device acting as a transmitter to an externally arranged receiver, as described in the international patent application PCT/SE2006/001135, assigned to Micropos Medical AB, which is hereby incorporated as reference. The transmitter transmits an electromagnetic signal at a specified frequency which is received at a plurality of receiving elements in the receiver. The receiving elements are typically arranged in a plane on a treatment table under a patient in which the positioning device is implanted. The communication uses near field transmission, and magnetic coupling is used between the transmitter and receiving elements. Parameters, such as amplitude and/or phase information, are measured from all receiving elements, preferably more than three receiving elements. These measurements are used to determine the position of the implantable positioning device.

All types of positioning systems need to be tested and verified in order to estimate the 3D position of an implantable positioning device within a body. Performance verification may be achieved by arranging the implantable positioning device at one predetermined position within a phantom that has the same electrical properties as the human body tissues at the specific frequency, and arranging the phantom above the receiver. The selected parameter(s) of the received signal at each receiving element is/are measured and compared with the expected parameter(s) for the predetermined position. If no discrepancy then performance verification is achieved, and if there is a deviation for one or more receiver elements adjustment of the receiver elements is required to eliminate the deviation.

The adjustment is rather coarse, and thus the accuracy of the positioning system is limited. Furthermore, the performance verification process is time consuming and a complex process that will occupy the radiotherapy equipment at regular intervals, which in turn will reduce the number of patients that could have been treated.

SUMMARY OF THE INVENTION

An object with the present invention is to provide a positioning system that more accurately may determine the position and orientation of a positioning device when arranged within a body.

A solution to this object is achieved by a model based positioning system that comprises a positioning device having at least one transmitter configured to be inserted into a body, a receiver having a plurality of receiver elements arranged outside the body, a control unit configured to measure amplitude and/or phase information of a signal transmitted from the at least one transmitter and received at each receiving element, and a memory unit for storing a model for each receiving element. The control unit is also configured to estimate the position of the positioning device by comparing the model for each receiving element with the measured received signal for each receiving element.

The stored model for each receiving element is created using the model based positioning system with the positioning device arranged at multiple known positions within a phantom having the same electrical properties as the human body tissues. Furthermore, the control unit is also configured to build a model comprising at least one of said plurality of receiving elements based on measured amplitude and/or phase information for each known position.

The object is also achieved by a method for tracking a position of a positioning device within a body and a method for calibrating the system used for tracking a position of a positioning device.

An advantage with the present invention is that a fast and accurate position of a positioning device may be obtained compared to prior art systems.

An advantage with a preferred embodiment is that a continuous performance verification process may be achieved by providing a reference transmitter arranged at a predetermined distance from each receiver element. A reference transmit signal is transmitted from the reference transmitter and a receive signal is measured at each receiving element, wherein the measured receive signal is weighted to coincide with a reference model obtained earlier.

Further objects and advantages will be apparent for a skilled person from the following detailed description.

DETAILED DESCRIPTION OF PREFERRED EMBODIMENTS

The detailed description will describe a model based positioning system that operates in two different modes. In a first mode, calibration mode, a model is built that reflects the impact of each receiver element when arranging a positioning device in an arbitrary position, and in a second mode, tracking mode, the built model is used to estimate the position of the positioning device.

A theoretical model could be built to allow direct calculation of the position of the positioning device from input data. However, this model will be quite complex in order to take all second order effects into consideration. Also, it requires that all second order effects and disturbances are both known and modelled. Examples of secondary effects are: surroundings (metal objects in the vicinity), mutual coupling between antenna elements, reflections of transmit signal at tissue/air interface, multilayer internal multi reflections (due to multiple tissue with different electrical properties), receiver antenna misalignment, near field propagation effects and interference/noise.

In the present patent application a different route has been taken comprising a data mapping procedure that uses calibration measurements to compare with measurements taken during tracking of a positioning device. This requires an accurate set of calibration measurements rather than a theoretical model. These calibration measurements are preferably stored in a database.

The advantages are several since it automatically takes all effects into consideration, such as receiving antenna misalignment, near field propagation effects, etc. It is very flexible and handles system that changes easily since the model is created from measurement data rather than theoretical analysis.

Calibration mode is achieved by arranging the positioning device in multiple known positions, belonging to a measurement range, within a phantom having the same electrical properties as human body tissues when an electromagnetic signal is transmitted from at least one transmitter within the positioning device at a specific frequency, e.g. ISM frequency −13.56 MHz. The model is built for each receiver element based on measurements of parameter values, such as amplitude and/or phase information, at the multiple known positions.

Tracking mode is achieved by inserting the positioning device into a body, and the signals received by the receiver elements is compared with each model with special search algorithms and a position is estimated.

The measurement range is at least 3 dimensional within the phantom, and is preferably selected to be larger than the area within which the implantable positioning device will be arranged during tracking mode. This is illustrated in FIGS. 1a and 1b.

Figure 1A:
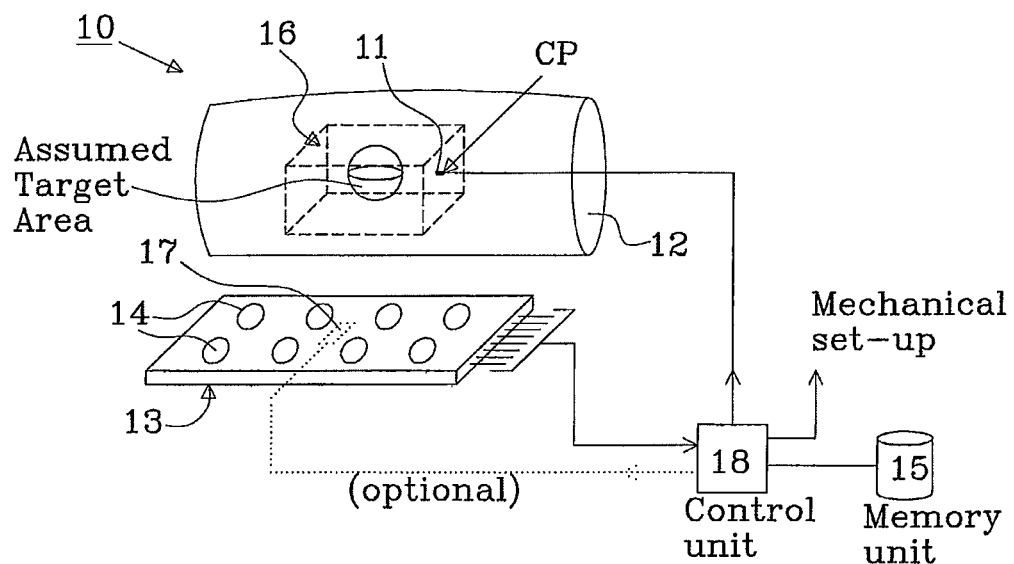
FIG. 1a shows a first embodiment of a system according to the invention during calibration.
Figure 1B:
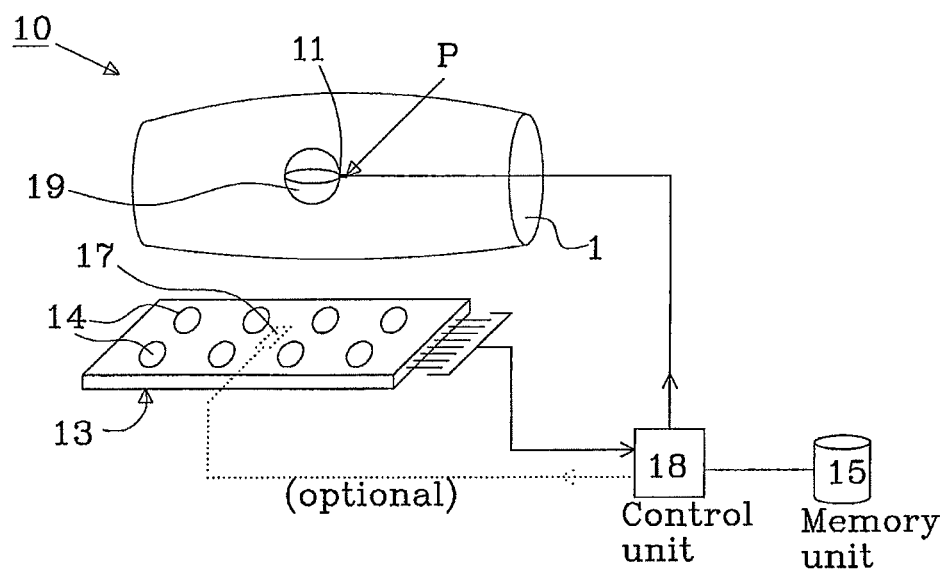
FIG. 1b shows a first embodiment of a system according to the invention during tracking.

FIG. 1a shows a first embodiment of a system 10 according to the invention during calibration mode. A positioning device 11 is inserted in a phantom 12, having the properties as discussed above, and is placed at a first calibrating position CP, which is known to the system, within a measurement range 16 illustrated by the dashed lines. A receiver 13 is arranged outside the phantom 12, said receiver comprises in this example eight receiver elements 14 which are connected to a control unit 18. A memory unit 15 is also connected to the control unit 18. An electromagnetic signal is generated in the control unit 18, which electromagnetic signal is transferred to the positioning device 11 inside the phantom 12, and the electromagnetic signal is transmitted from one or more transmitters (not shown) in the positioning device 11 at the first calibrating position CP. Each receiving element 14 receives a signal which is transferred to the control unit 18 and parameter values, such as amplitude and/or phase information for the received signal at each receiver element is thus measured. Data containing the parameter values for each receiver element 14 together with information regarding the first calibrating position CP are thereafter stored as a database in the memory unit 15.

Figure 4:
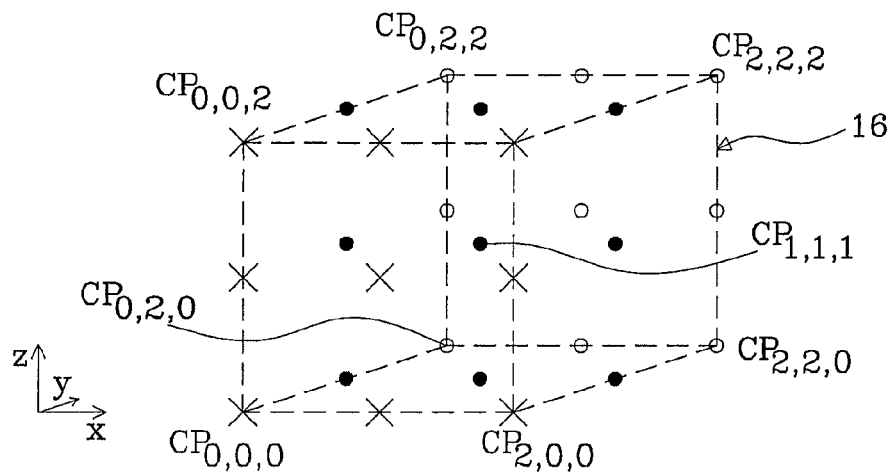
FIG. 4 shows a calibration mode set-up.
Figure 5:
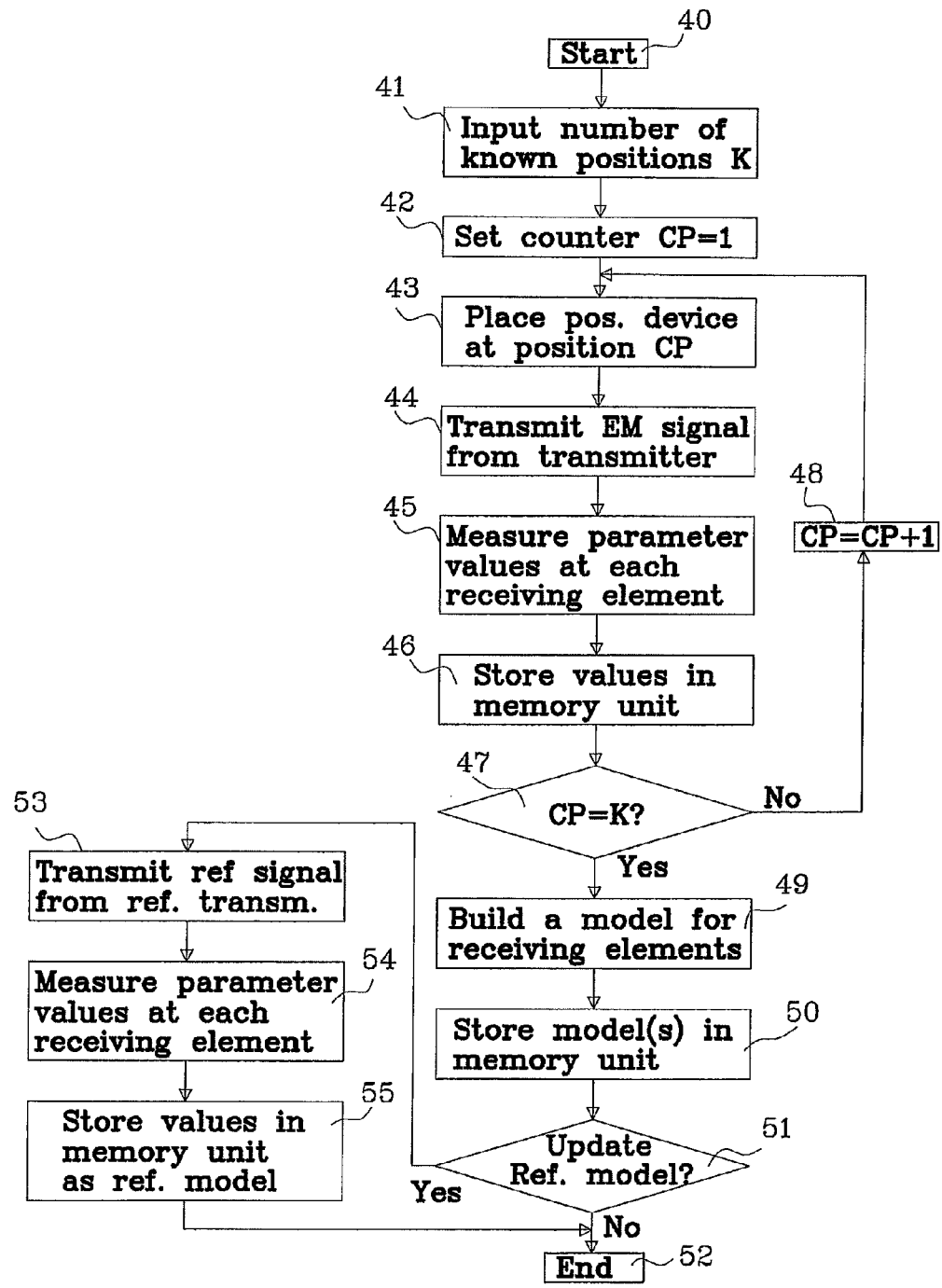
FIG. 5 shows a flow chart for calibrating the system according to the invention.

The positioning device 11 is then moved to another calibration position within the measurement range 16 and the process is repeated, as illustrated by the flow chart in FIG. 5. A model for each receiving element 14 is build based on the stored data in the database of the memory unit 15. All calibrating positions (CPs) are known to the system and are preferably equally spaced in the entire measurement range 16, and the database is preferably created using the system 10 with a mechanical set-up (not shown) that can accurately move the positioning device in position, and optionally orientation, as discussed in connection with FIGS. 3 and 4, by computer control. The control unit 18 will send a control signal to the computer to move the positioning device 11 to the next known calibrating position when the data from the previous calibrating position has been stored. It is of course possible to move the positioning device by hand, when prompted by the control unit, or a positioning device may be placed at each calibrating position within the measurement range 16 and the control unit switches between the positioning devices at the different calibrating positions.

The system 10 may be provided with an optional reference transmitter 17 connected to the control unit 18, as indicated by the dotted line. The purpose of the reference transmitter 17, which transmitter may or may not be an integral part of the receiver 13, is to monitor the wear and tear of the receiving elements 14 due to exposure to radiation during radiotherapy, and adapt the receiver to a new environment where other electromagnetic fields may influence the operation of the receiving elements, or adjust the receivers for temporary disturbances, such as the presence of a metal plate. The reference transmitter has a predetermined distance to each receiving element 14 that will not change over time.

To achieve this purpose, a reference model needs to be established, preferably at the same time as the model for each receiving element 14 is built. A reference transmit signal is created in the control unit 18 and transferred to the reference transmitter 17, wherefrom an electromagnetic reference signal is transmitted and received by each receiving elements 14. The reference model, which preferably comprises amplitude and/or phase information measured by the receiving elements 14, is stored in the memory unit. It is of course possible to use more than one reference transmitter to further improve the accuracy of the reference model.

FIG. 1b shows a first embodiment of a system 10 according to the invention during tracking mode. The positioning device 11 has been arranged in relation to a target area 19, e.g. cancer, inside a body 1, e.g. a patient that is about to be exposed to radiation during a radiotherapy treatment. The positioning device 11 is positioned at an unknown position P, which is to be determined.

The control unit 18 creates an electromagnetic signal, which is identical to the signal used during calibration and transfers it to the transmitter(s) inside the positioning device 11. The signal transmitted from the positioning device 11 is measured at each receiving element 14 and the same parameter values of the received signals, as measured during calibration, is stored in the memory unit 15, or in an internal memory (not shown) of the control unit 18. The control unit retrieves the model for each receiving element 14, obtained as described above, and estimates the position P of the positioning device 11 by comparing the retrieved models with the measured receive signal for each receiving element 14. This process is described in more detail in connection with the flow charts in FIGS. 6 and 7.

If a reference transmitter 17 is present, a continuous monitoring process may be performed, as described in more detail in connection with the flow chart in FIG. 8.

The electromagnetic signal that is generated in the control unit 18 is adapted to propagate with a wavelength in the phantom 12/body 1, and, in a first example, a phase difference of the electromagnetic signal is detected by the receiving elements 14 arranged outside the phantom 12/body 1. The wavelength is selected so that a distance from the transmitter(s) in the positioning device 11 to each of the receiving elements 14 is within the same integer number of wavelengths of the electromagnetic signal, in such a way that they operate in a near field region. A prior art detector system is described in an international patent application PCT/SE05/000646, assigned to Micropos Medical AB, wherein a transmitter arranged in relation to a target area inside a body transmits a signal having a frequency within the range of 5-350 MHz, and a phase difference from the transmitted signal is detected by a receiver at three, or more, positions to track variations in position of the transmitter.

The prior art system described defines a transmitter and a multiple of receiving antennas that operates in a near field region. The behaviour of an electromagnetic signal in the near field region is known for a skilled person and is described in a publication with the title "Near field Phase Behavior", by Hans Gregory Schantz, IEEE APS Conference July 2005. In this publication the author presents a reprint of a plot published in "Electric waves", by Heinrich Hertz, London, Macmillian & Co. 1893, page 152 and a plot, shown in FIG. 9, was published by Q-track in 2004.

Figure 9:
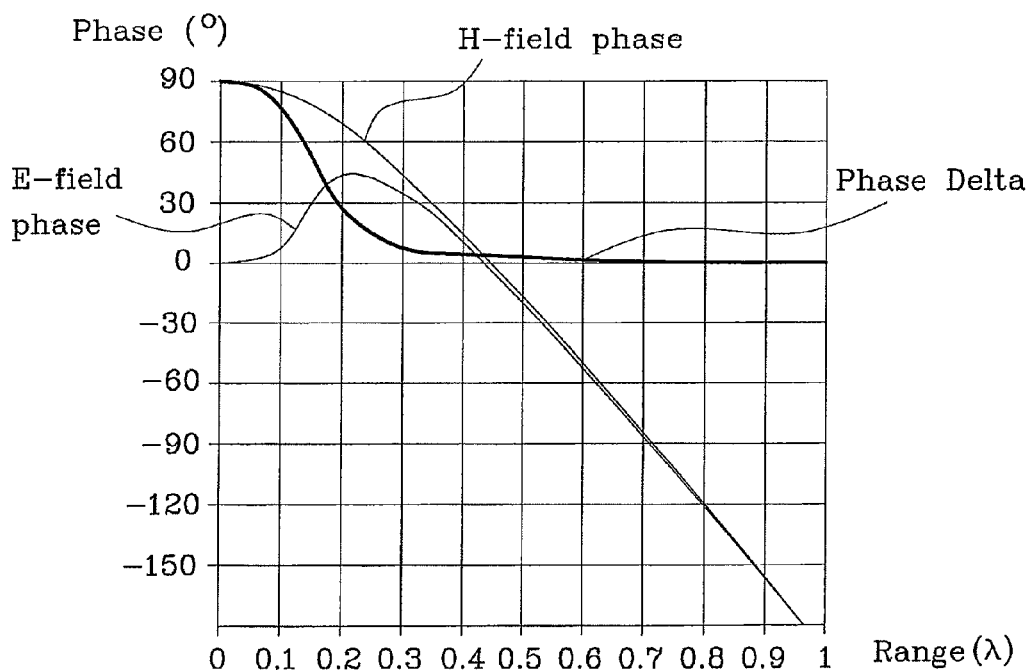
FIG. 9 shows a plot illustrating the near field effect of electromagnetic signals.

The plot describes the phase behaviour of the magnetic field (H-field) and the electrostatic filed (E-field) below one wavelength of an electromagnetic signal. In this near field region of an antenna, the magnetic field and electrostatic field phases radically diverge, and in a far field region, many wavelengths away from a transmit antenna, the magnetic and electrostatic field move with perfect synchronized phase. FIG. 9 illustrates the effect of the near field region, and the phase delta between the magnetic field and electrostatic field at zero $\lambda$ is 90 degrees, which decreases to a phase difference of 0 degrees at one $\lambda$.

The separation of the magnetic field and the electrostatic field in the near field region opens up a number of possibilities to construct improved measurement systems. The shape of the wave front of the electromagnetic signal may be used to determine the distance between the transmitter and the receiver. It is also advantageous to increase the sensitivity of the measurement system by introducing electrostatically shielded antennas, which is possible since the magnetic field and electrostatic field are separated in the near field region, whereby the magnetic field is used to determine the variations of the position of the transmitter.

A more detailed description of the detector system may be found in the international patent application with the application number PCT/SE05/000646, which is hereby incorporated by reference.

In a second example, amplitude difference of the electromagnetic signal is detected instead of the phase difference as described above. A transmitter arranged in relation to a target area inside a body transmits a signal having a frequency within the range of 1 kHz-350 MHz and an amplitude difference from the transmitted signal is detected by a receiver at three, or more, positions to track variations in position of the transmitter. The amplitude of the magnetic field is preferably measured when operating in near field, for instance by measuring absolute value or mean value of the magnetic field.

It is of course possible to combine the above described examples and use both phase and amplitude difference to determine variations of the position of the transmitter in the positioning device 11.

Figure 2:
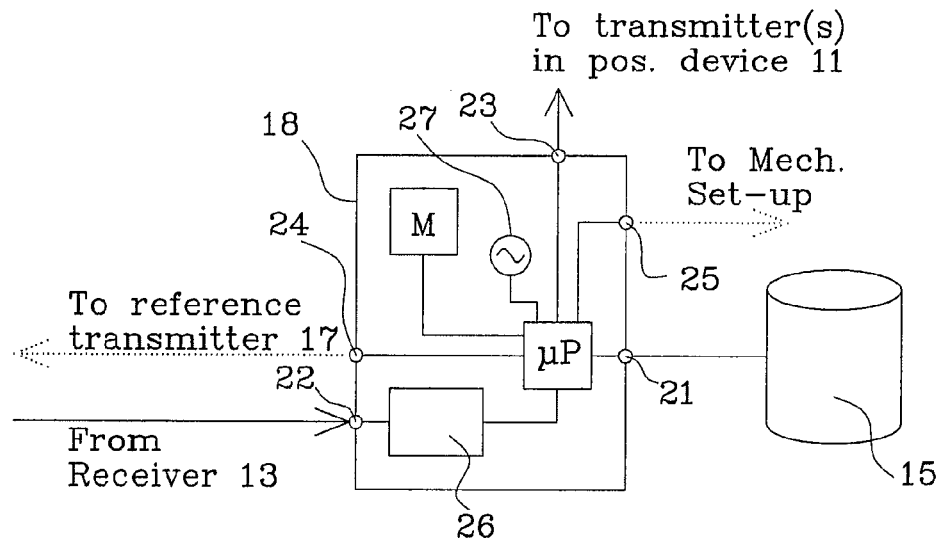
FIG. 2 shows a control unit configured to be used in the system according to the invention.

FIG. 2 shows the control unit 18 configured to be used in the system 10 according to the invention. The control unit 18 comprises a microprocessor μP, an internal memory M, and a parameter value detector 26 in which one or more desired parameter values, such as amplitude and/or phase information, of each received signal are extracted from the receive signals. The memory unit 15 is connected to the microprocessor μP through a two-way communication port 21, and the signals received at the receiving elements 14 of the receiver 13 are connected to the parameter value detector 26 through an input port 22. The parameter values are thereafter transferred to the microprocessor and stored in the memory unit 15.

One transmit signal for each transmitter present in the positioning device 11 is generated in the control unit 18 using an electromagnetic signal source 27, which is controlled by the microprocessor μP, and is transferred to the positioning device 11 through an output port 23. The internal memory M is connected to the microprocessor μP and the software that controls the microprocessor is stored there, and the memory may also be used to temporarily store data during processing.

The control unit 18 is also provided with the optional output ports. A reference transmit signal, to be transmitted from the optional reference transmitter 17, is generated in the control unit 18 using the electromagnetic signal source 27 controlled by the microprocessor μP, and is transferred to the reference transmitter 17 through a first optional output port 24. If the control unit 18 is adapted to control a mechanical set-up to ensure that the positioning device is moved between known calibrating positions CP during the calibration procedure, a control signal is provided to the mechanical set-up through a second optional output port 25.

The transmitter(s) is/are preferably continuously transmitting a sine wave signal. Measurements are taken from all receiving elements as amplitude, and possible phase information. These measurements are used as input to the system process as described below.

Figure 3:
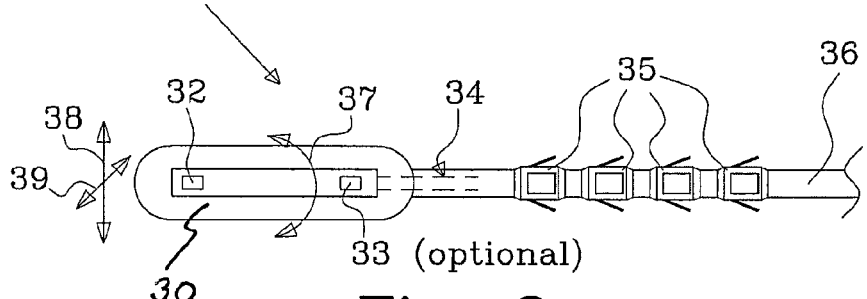
FIG. 3 shows an implantable positioning device used in the system according to the invention.

FIG. 3 shows an example of an implantable positioning device 31 that could be used in the system 10 according to the invention. In this example a separate outer cover, such as a catheter, is not provided. A transmitter 32 is provided, together with an optional transmitter 33, in a biocompatible capsule 30, and transmission lines 34 connecting the transmitters 32, 33 with an external control unit (not shown) are contained within a biocompatible lead 36. In this example, the fastening means are implemented as a multiple of tine elements 35, in this example four elements, arranged on the outside of the lead 36. Further examples of tine elements may be found in the published US application US 2006/0129218, assigned to Medtronic, Inc.

The task of the system described above is to provide a vector of measurement values originating from the radio transmission and produce an estimated position in Cartesian coordinates. This position is in three dimensions (x,y,z), as illustrated in connection with FIG. 4, but in practise the positioning device will also rotate in three additional dimensions. To guarantee position accuracy, also when the positioning device is rotated, rotation must be taken into consideration during calibration mode, even though rotation may not be presented to the user of the system or included in the error estimates.

Normally, the positioning implant is rotationally symmetric along one axis, see arrow 37, and therefore only two rotations normally need to be taken into consideration during the calibration process, arrow 38 indicating an elevation angle and arrow 39 indicating an azimuth angle.

Therefore, each calibrating position includes a 5 (or possibly 6) dimensional output (a 3 dimensional position in space and 2-3 rotations) from the radio transmission measurements FIG. 4 shows a calibration mode set-up defining a measurement range 16 with all calibrating positions $CP_{0,0,0}$-$CP_{2,2,2}$, equally spaced, within the measurement range 16. For illustrating purposes, the calibrating positions with y=0 are indicated by crosses, y=1 are indicated with dots, and y=2 are indicated by circles.

In the simplest calibration process only Cartesian coordinates x,y,z are used as calibrating positions, whereby only 27 ($3^3$) known calibrating positions are used to cover the measurement range. In a preferred embodiment at least two rotations are included at each Cartesian coordinate, e.g. by adding three different angular positions in both elevation and azimuth, as indicated by arrows 38 and 39 in FIG. 3. The inclusion of two rotations will increase the number of calibrating positions to be 243 ($3^5$), and by also adding axis rotation at three different angular positions, as indicated by arrows 37 in FIG. 3, the number will increase to 729 ($3^6$) known calibrating positions.

The stored parameter values in the memory unit 15 comprises preferably of equally spaced measurement points in the entire measurement range, and a database is created by using the described system preferably with a mechanical set-up that can accurately move the positioning device in position (Cartesian coordinates) and orientation (rotations) by computer control. This may be performed in air or water (preferably with specific concentration of saline solution to closely mimic the human body with regard to electrical properties). Typically six measurement points are selected along each axis, resulting in a total number of 7776 calibrating positions ($6^5$) for a 5 dimensional output (three Cartesian coordinates+two rotations). All the measurements made at each calibrating position constitute the database. Each database entry consists of the calibrating position (5 dimensional position/orientation) and a radio transmission measurement vector (1-2 values per receiving element 14).

FIG. 5 shows a flow chart for calibrating the system 10 according to the invention. The flow starts at step 40, and the number K of known positions is fed into the system in step 41. In the example illustrated in connection with FIG. 4, K=243 for a 5 dimensional output. A counter for the calibrating position (CP) is set to one in step 42, CP=1. The positioning device is thereafter placed in the first calibrating position (CP=1) in step 43. This step is preferably performed by a computer being controlled by the control unit, as described in connection with FIG. 2.

An electromagnetic signal is thereafter transmitted to the transmitter placed within the positioning device in step 44. If more than one transmitter is present, each transmitter transmits a unique electromagnetic signal. Parameter values, such as amplitude and/or phase information, are thereafter measured at each receiving element in step 45. The number of receiving elements is preferably 8-12, as described above. The parameter values are stored in the memory unit in step 46, and in step 47 the calibrating position CP is compared with K. If CP≠K, then the flow is fed back to step 43 via step 48, wherein the value of CP is increased by 1, i.e. CP=CP+1. Steps 43-47 are repeated until CP=K in step 47, and at least one model is built containing information from each receiving element in step 49. A separate model for each receiving element is preferred. Step 49 is explained in more detail below. The model(s) is/are stored in the memory unit 15, or in the internal memory M of the control unit 18 in step 50.

If no reference transmitter 17 is present, the flow will end in step 52 and the calibration process is completed. If another calibration process needs to be performed, e.g. during verification or service of the system, the flow starts at step 40.

If a reference transmitter 17 is present, an option to update the reference model is presented in step 51. If no update is desired the flow ends at step 52, and when an update of the reference model is selected, the flow continues to step 52. A transmit reference signal is created in the control unit and transmitted from the reference transmitter in step 52. Parameter values are measured at all receiving elements 14 in step 53, and the values are stored in the memory unit 15, or in the internal memory M, as a reference model, in step 54. The flow ends in step 52.

The database comprising the stored parameter values for each receiving element at each calibrating position may be used as a model for each receiving element 14, but to speed up the estimation process, as described in connection with FIGS. 6 and 7, and provide some level of data filtering, the database is converted to a model. This model is based on mathematical entities that easily may be used to calculate each calibration transmission measurement from the calibrating position data 8, e.g. 5 dimensional position/orientation data. Polynomials are preferably used, wherein one polynomial for each transmission vector entry is calculated.

In one embodiment, the polynomial has a 5 dimensional input and is of a typical order of 4, and thus has 3125 coefficients. It has been shown that polynomials rather accurately map the measurements in the database, and increasing the order does not significantly improve performance. An advantage in using polynomials with an order of 4 is that data filtering may be performed, since there normally are more measurements (7776 calibrating positions) to use than coefficients (3125) to solve. Using an order that is one less than the number of points taken along each axis when creating the database will yield an exact solution at the database points (calibrating positions), and polynomial interpolation between the database points. The choice of using one order less provides a possibility to perform data noise filtering and lessens the computational burden significantly.

The mathematics to extract the model (polynomial coefficients) from the database is straightforward. The relationship between the measurements on one side, and the polynomial coefficients and position/orientation on the other side forms a linear equation system. This linear equation system may be solved by readily available methods to solve the polynomial coefficients. A least square, or Monte Carlo, methods may be used to optimize the data fitting when the linear equation system is over determined as in the above described case. This process provides the data noise filtering mentioned above. As a practical approach, the process for building the models may be implemented in Matlab software, and the "backslash" operator is used to easily solve the linear equation system.

When a model is built for each receiving element 14 in the receiver 13, the system is ready to be used to estimate an unknown position of a positioning device arranged in an environment with similar electrical properties as in the measurement range 16 during calibration, e.g. inside a phantom 12.

Figure 6:
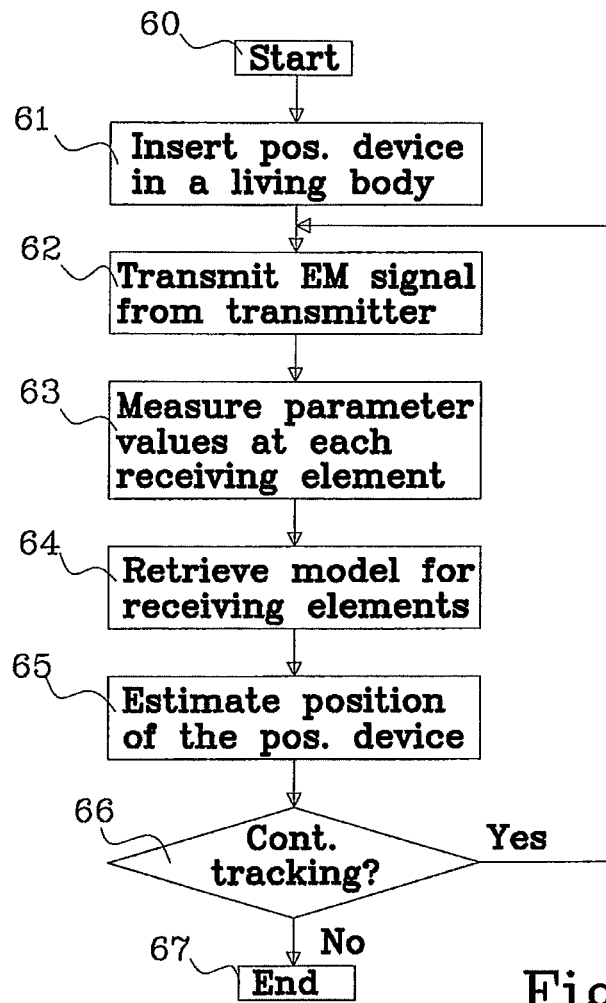
FIG. 6 shows a flow chart for tracking a positioning device in a system according to the invention.

FIG. 6 shows a flow chart for tracking a positioning device in a living body using a system according to the invention. The flow starts in step 60, and a positioning device is inserted in the living body in step 61. It should be noted that the procedure to insert the positioning device in the living body may be performed by any person, even the patient herself, using a natural opening, such as the urethra.

An electromagnetic signal is transmitted from each present transmitter in the positioning device in step 62 and parameter values, such as amplitude and/or phase information is measured at each receiving element in step 63. These steps are identical to step 44 and 45 in FIG. 5. In step 64, the models for the receiving elements are retrieved from the memory unit 15, or from the internal memory M of the control unit 18. The position of the positioning device is estimated in step 65, which step is described in more detail below. If a continuous tracking of the positioning device is desired the flow is fed back to step 62 via step 66, if not the flow ends in step 67.

Each retrieved model provides a quick and easy way of calculating a transmission measurement vector from position/orientation data, but when performing a position estimate the process is reversed, i.e. from a transmission measurement vector to a position/orientation estimate. This may be done by performing a search in the measurement range to find a position that is close enough. This search is performed in two stages, a global and a local search, as illustrated in FIG. 7.

Figure 7:
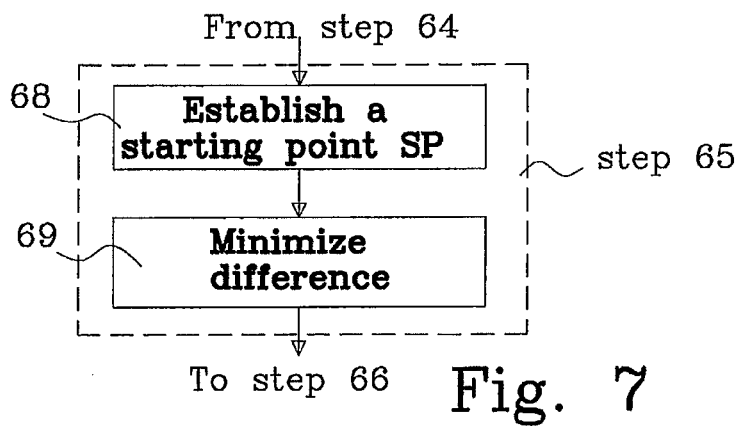
FIG. 7 shows a detailed flow chart for estimating the position of the position device.

FIG. 7 shows a detailed flow chart for estimating the position of the position device. The flow from step 64 continues to step 68, where a global search is performed. The global search tries a number of equally spaced points (calibrating positions) in the entire measurement range (5 dimensional position/orientation). This search finds the correct area in the measurement range and establishes a good starting point SP for the local search to follow. The target for the search procedure is to minimize the difference between the transmission measurement vector taken, and the corresponding vector calculated using each model from the current starting point.

The local search is performed in step 69, and uses the result from the global search as a starting point SP. For each iteration, it moves a small step along each direction of each axis in order to minimize the measurement vector difference. The local search keeps the movements that actually decrease this difference. For each iteration, the step length is decreased to take smaller and smaller steps. The search is terminated when the step length is small enough compared to the system resolution requirements.

Figure 10:
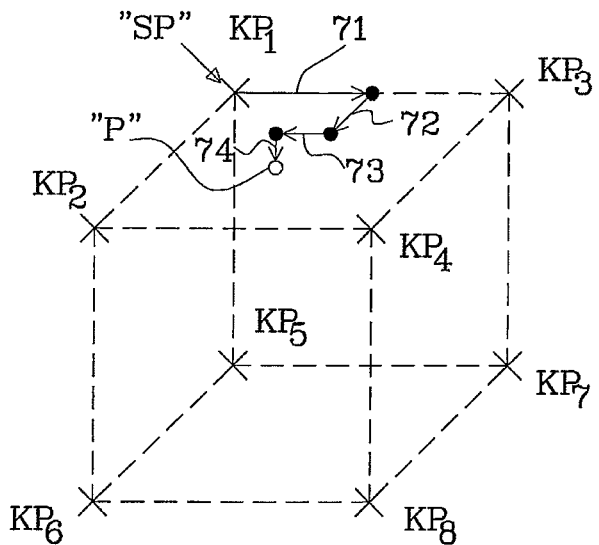
FIG. 10 shows the iterative process for establishing the position of a positioning device.

This process is described in connection with FIG. 10. A number of known positions $KP_1$-$KP_8$ are illustrated by crosses. One of the known positions has been determined to be the starting point "SP" as described above in step 68. The iterative process to minimize the difference in step 69 is illustrated by the arrows 71-74. The lengths of the arrows are indicative of the step size, which is reduced between each iteration. The final point "P" is determined to be the position of the positioning device when the step length is smaller than the required resolution.

Figure 8:
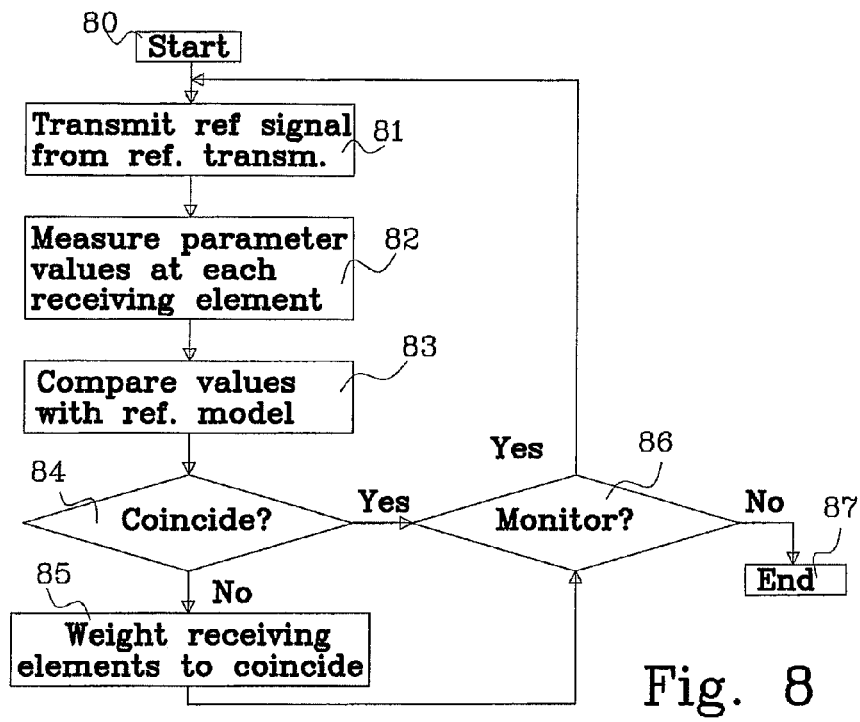
FIG. 8 shows a flow chart for monitoring the function of the receiving elements during operation.

FIG. 8 shows a flow chart for monitoring the function of the receiving elements 14 during operation. If the system is provided with a reference transmitter, either integrated with the receiver 13 or as a separate unit, the system may perform a system check that will ensure that the receiving elements are operational. This procedure may be conducted parallel with the tracking of the positioning device as described in FIGS. 6 and 7.

The flow starts in step 80, and a transmit reference signal (identical to the transmit reference signal used for building a reference model as described in connection with FIG. 5) is transmitted from the reference transmitter in step 81. Parameter values are measured at all receiving elements 14 in step 82, and the values are compared with the reference model stored in the memory unit 15, or in the internal memory M, in step 83.

If the parameter values coincide, step 84, no further actions are taken and the flow continues to step 86. However, if they do not coincide in step 84, the flow continues to step 85, wherein the output from the receiving elements 14 are weighted in order to make them coincide. The weighting is stored in the internal memory M and the flow continues to step 86. If the monitoring of the receiving elements shall continue, the flow is fed back to step 81 and steps 82 to 86 is repeated, or else the flow ends in step 87.

More than one reference transmitter is naturally possible, whereby a redundancy in the monitoring of the receiving elements is achieved.

Figure 11:
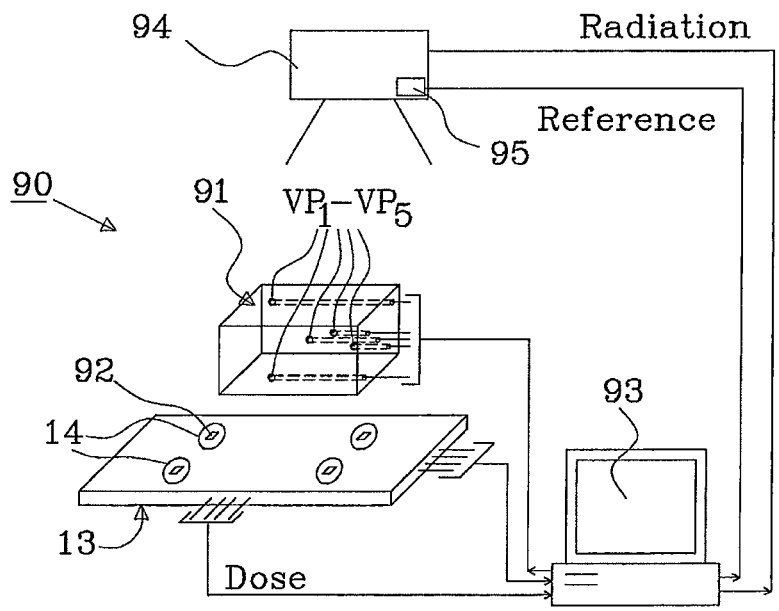
FIG. 11 shows a second embodiment of a system according to the invention during verification.

FIG. 11 shows a second embodiment of a system 90 according to the invention during verification. Verification transmitters are installed in a verification kit 91 in preselected verification positions $VP_1$-$VP_5$ as illustrated in FIG. 11. When a transmit signal is transmitted from the verification transmitters in the verification kit 91, parameter values are measured at the receiving elements 14 and compared to previously stored values. If these are within a preselected measurement interval, the system is ok and a patient may be coupled to the system.

A dose sensor 92 is also provided close to each receiving element 14 in the receiver 13. The measured dose at each dose sensor 92 is measured and stored in a computer 93, which also is configured to handle the tasks performed by the control unit 18 described above. Receive signals from the receiving elements 14 is thus measured and parameter values are stored in an internal computer memory or in an external database, as described above. The transmit signal to the verification transmitters (as well as transmit signals used in calibration mode or tracking mode) are controlled by the computer 93. The dose sensors 92 may be used to monitor the amount of radiation that each receiving element 14 is exposed to. The radiation is emitted from a radiation source 94 during radiotherapy treatment of a patient. The purpose of the dose sensor is thus to be able to predict when a receiving element needs to be replaced when being exposed to more than a predetermined radiation dose, e.g. 3 Gray.

Furthermore, a reference transmitter 95 is provided near the radiation source 94. By avoiding the reference transmitter 95 to be exposed to radiation, the reference transmitter 95 is not affected by the radiation in the same way as the receiving elements 14 are. The position of the radiation source 94 in relation to the receiver 13 may be controlled by the computer to ensure that the reference transmitter 95 is placed in a predetermined position whenever the reference transmitter is active.

One of the fundamental criteria for being able to perform the present invention is that the same type of positioning device is used both for calibration mode and tracking mode. If several types of positioning devices are used in the same system, models for each type of positioning device have to be stored in the memory unit (or internal memory), and the system needs to be informed of which type of positioning device that are used during tracking mode to be able to function properly. This information may naturally be included in a memory within the positioning device, as have been described in the international patent application PCT/2006/001242 assigned to Micropos Medical AB, which is incorporated as reference.

The same verification kit needs to be used every time when verifying the operational status of the system. If any part of the verification kit is exchanged/replaced a new base line verification needs to be performed.

Figure 12A:
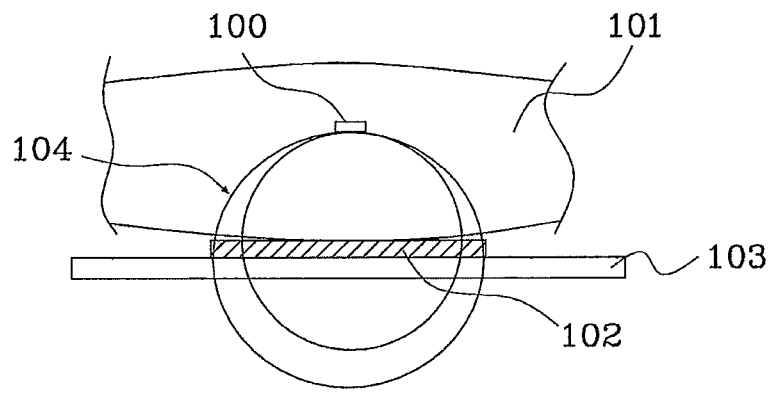
FIGS. 12a-12c schematically illustrates the use of a system according to the invention with a treatment table during operation.
Figure 12B:
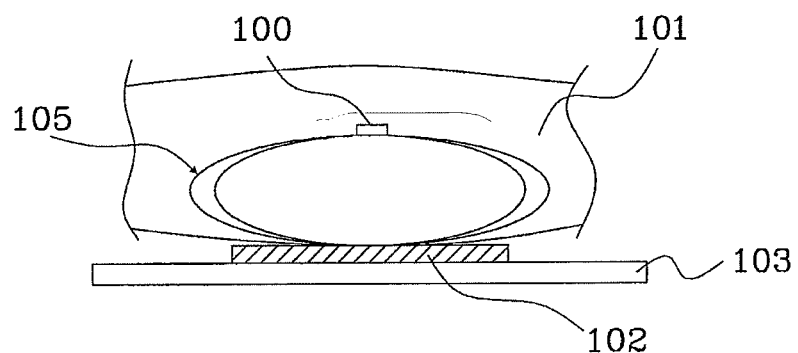
Figure 12C:
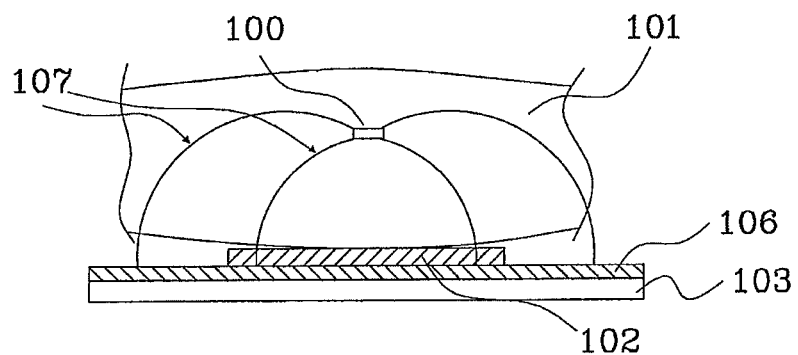

FIGS. 12a-12c illustrate the use of a positioning system with a treatment table during operation.

A standard treatment table is normally made from a conductive material (having a conductivity larger than zero Siemens/meter: σ>0 S/m), such as carbon fiber, metal etc. and prior art positioning system need a treatment table made from a non-conductive material (having a conductivity equal to zero Siemens/meter: σ=0 S/m) to function properly. The reason for this is based on the fact that a disturbance will occur when placing a receiver and/or transmitter close to conducting surfaces.

Receiver antennas are disturbed in such a way that their resonant frequency changes close to conducting surfaces/environments, and the amplitude of the received signal is attenuated due to eddy currents. Eddy current problem is the most critical part of prior art systems. The receiving antennas may be trimmed to compensate for the resonant frequency change in the receiver antennas, but eddy current on the other side attenuates the received signal strength and this is critical for making beacons to be operable.

A transmitting antenna is also disturbed in such a way that their resonant frequency is changed close to conducting surfaces/environments, and the eddy current amplitude of the signal needed to power up a wireless beacon (which is normally used in prior art systems) is attenuated.

A wireless prior art beacon can not be controlled once it has been inserted into a body. A beacon does not include a power source on their own, which means that they need to be powered from the exterior. When the signal that should excite beacons is not strong enough (due to eddy currents) they are inoperable. The implantable positioning device according to the invention is connected through a wire to the system and power source which enable trimming and adjustments to compensate for all kinds of disturbances that different environments can cause.

Amplitude of the received signal is attenuated and in a system based on amplitude measurements, the system will not work due to the fact that the received signal from the transmitter antennas is too weak. A solution to this problem is to measure phase instead, but it is not possible to measure phase of a signal which is undetectable due to its weakness. The only option left is to construct a treatment table made of a non-conducting material as illustrated in FIG. 12a.

FIG. 12a shows a treatment system with an implantable positioning device 100 positioned within a body 101. The body is placed on top of a receiver plate 102 comprising multiple receiver antennas (not shown), and the receiver plate 102 is placed on a treatment table 103 made from a non-conducting material (σ=0). The magnetic field (H field) is illustrated by the field lines 104.

FIG. 12b illustrates the eddy current effect of the system disclosed in FIG. 12a when the treatment table 103 is made from a conducting material (σ>0), such as carbon fibers, metal, etc. It should be noted that it is still possible to register the signal/communication between the implantable positioning device 100 and the receiver antennas. However, due to the fact that the magnetic field lines 105 runs parallel to the receiver plate 102 all receiver antennas will experience the same amplitude for different positions of the implantable positioning device 100. It is therefore impossible to build a model for implant positioning since the database will contain the same amplitude vectors that do not differ dependent on the position of the implantable positioning device 100.

The above described problem with eddy currents is a well-known problem for RFID applications. In a publication from TDK Corporation with the title "Flexible Composite-Type Electromagnetic Shield Material For The 13.56 MHz-Band RFID System", which is incorporated by reference, the problem caused by eddy currents is described. As TDK describes, one way of solving this problem, i.e. to cancel the effect of eddy currents, is to use a ferrite material interposed between the conducting surface and the antenna. Once a ferrite material is interposed, the orientation of the magnetic field lines may be controlled in such a way that makes the system operable. Furthermore, the material in the treatment table is no longer of importance since the ferrite material acts like a shield, as illustrated in FIG. 12c.

FIG. 12c shows a treatment system in which the effect of the eddy current has been cancelled. A shield 106 made from a ferrite material (having a permeability larger than one: $\mu>1$) is interposed between the receiver plate 102 and the treatment table 103, which could be made from a conducting (or non-conducting) material. The magnetic field lines 107, being perpendicular to the shield 106 will cause the magnetic field lines to be more or less perpendicular to the receiving antennas in the receiver plate 102.

In an alternative embodiment, the shield 106 may be replaced by, or combined with, a mirror plane (preferably made from a sheet of aluminium) built into the receiving plate 102. The purpose of the mirror plane is to make the magnetic field lines to be more or less perpendicular to the receiving antennas in the receiver plate. The mirror plane will effectively cancel the eddy current effect described above. Both the shield made from the ferrite material and the mirror plane will create magnetic field lines being non-parallel to the receiver plate, and thus the position of the implantable positioning device may be determined according to the invention.

Different objects could cause disturbances in the system, such as an operator close to the system during operation. These disturbances are more of a capacitive nature and are omitted by the inventive system since electrostatically shielded antennas are used which cancel only the electrostatic field when operating in a near field region of the antenna.

What is claimed:

1. In a system for medical treatment utilizing tracking of a position within the body of a patient undergoing treatment, a method for calibrating a position determining system used for tracking the position of a positioning device configured to be placed inside the body of the patient, said method comprising the steps:
   a) placing the positioning device at a known position in a phantom having a calibrating environment with predetermined electrical properties, said positioning device comprising at least one transmitter configured to be placed inside said body of the patient, b) transmitting an electromagnetic transmit signal at a specified frequency from each transmitter, c) providing a receiver comprising a plurality of electrostatically shielded receiving elements arranged outside the phantom, and measuring a receive signal transmitted by said b) transmitting at each receiving element, said transmitter(s) and receiver operating in a near field region, and d) storing data regarding the known position of the positioning device, and amplitude and/or phase information for each measured receive signal in a memory unit, said method further comprising the steps:

repeating steps a)-d) for multiple known positions in the phantom, said known positions belonging to a measurement range, and building a separate model of the position of the positioning device for each receiving element based on the stored data for each known position in step d) to enable more accurate position measurement of position detection utilized during medical treatment; wherein the model is based on known positions in a measurement range and is performed by estimating the position using a two stage search procedure, a first stage comprising trying a number of equally spaced positions in the measurement range to establish a starting point in the model for each receiving element, and a second stage comprising minimizing a difference between a vector corresponding to the measured receive signals and a calculated vector corresponding to the starting point using an iterative search process.

2. The method according to claim 1, wherein said phantom is selected to have similar electrical properties as a body at the specified frequency of said transmit signal.

3. The method according to claim 1, wherein the positioning device comprises at least two transmitters, and each transmitter transmits a transmit signal at separate frequencies.

4. The method according to claim 1, wherein said step of building a model comprises the step of determining an amplitude and/or phase distribution for each receiving element.

5. The method according to claim 4, wherein said model is selected to be a polynomial.

6. The method according to claim 5, wherein data filtering is provided to further optimize data fitting when determining the polynomial.

7. The method according to claim 1, wherein said known position comprises three-dimensional coordinates and at least two rotations of the positioning device, resulting in at least five-dimensional data for each measured receive signal.

8. The method according to claim 1, comprising the further step of establishing a reference model for the receiving elements by:

transmitting a reference transmit signal from at least one reference transmitter being arranged at a predetermined distance from each receiving element, measuring a reference receive signal at each receiving element, and storing data regarding amplitude and/or phase information for each measured reference receive signal as the reference model in the memory unit.

9. The method according to claim 8, wherein the reference transmitter is selected to be arranged in said receiver.

10. In a system for medical treatment utilizing tracking of a position within the body of a patient undergoing treatment, a method for tracking a position of a positioning device configured to be placed inside of the body of the patient, said method comprising the steps:

arranging the positioning device in relation to a target area in a tracking environment, said positioning device comprising at least one transmitter, transmitting an electromagnetic transmit signal at a specified frequency from each transmitter, and providing a receiver comprising a plurality of electrostatically shielded receiving elements arranged outside the tracking environment, and measuring a receive signal at each receiving element, said transmitter(s) and receiver operating in a near field region, retrieving, from a memory, a separate model for each receiving element, obtained by a calibrating method comprising:

a) placing the positioning device at a known position in a phantom having a calibrating environment with predetermined electrical properties, said positioning device comprising at least one transmitter configured to be placed inside said body of the patient, b) transmitting an electromagnetic transmit signal at a specified frequency from each transmitter, c) providing a receiver comprising a plurality of electrostatically shielded receiving elements arranged outside the phantom, and measuring a receive signal transmitted by said b) transmitting at each receiving element, said transmitter(s) and receiver operating in a near field region, and d) storing data regarding the known position of the positioning device, and amplitude and/or phase information for each measured receive signal in a memory unit, wherein said calibrating method further comprising the steps:

repeating steps a)-d) for multiple known positions in the phantom, said known positions belonging to a measurement range, and building a separate model of the position of the positioning device for each receiving element based on the stored data for each known position in step d), wherein the model is based on known positions in a measurement range; and estimating the position of the positioning device by comparing the retrieved model for each receiving element with the measured received signal for each receiving element to more accurately determine position during medical treatment by performing a two stage search procedure, a first stage comprising trying a number of equally spaced positions in the measurement range to establish a starting point in the model for each receiving element, and a second stage comprising minimizing a difference between a vector corresponding to the measured receive signals and a calculated vector corresponding to the starting point using an iterative search process.

11. The method according to claim 10, wherein the tracking environment is selected to be inside a body.

12. The system according to claim 10, wherein said at least one transmitter transmits a signal having a frequency within the range of 1 kHz-350 MHz and an amplitude difference from the transmitted signal is detected by the receiver at three, or more, positions to track variations of the transmitter.

13. A system for medical treatment utilizing tracking of a position of a target area in a tracking environment, wherein said target area is located inside of a body of a patient, said system comprising:
- a positioning device configured to be arranged in relation to said target area, said positioning device comprising at least one transmitter,
- a receiver configured to be arranged outside said tracking environment, said receiver comprising a plurality of electrostatically shielded receiving elements, each arranged at a different location in said receiver, and
- a control unit in communication with said positioning device to initiate transmission of a transmit signal from said transmitter(s), said control unit being connected tq said receiver to obtain a receive signal from said at least one transmitter received by each receiving element,
- a memory unit connected to said control unit, said memory unit comprises a stored separate model of the position of said positioning device; wherein the model is based on known positions in a measurement range obtained by a calibrating method, for each receiving element, wherein said calibrating method comprises:
  - a) placing the positioning device at a known position in a phantom having a calibrating environment with predetermined electrical properties, said positioning device comprising at least one transmitter configured to be placed inside said body of the patient,
  - b) transmitting an electromagnetic transmit signal at a specified frequency from each transmitter,
  - c) providing a receiver comprising a plurality of electrostatically shielded receiving elements arranged outside the phantom, and measuring a receive signal transmitted by said b) transmitting at each receiving element, said transmitter(s) and receiver operating in a near field region, and
  - d) storing data regarding the known position of the positioning device, and amplitude and/or phase information for each measured receive signal in a memory unit,
- wherein said calibrating method further comprising the steps:
  - repeating steps a)-d) for multiple known positions in the phantom, said known positions belonging to a measurement range, and
- said control unit further comprising a computing unit adapted to estimate the position of said positioning device by comparing the stored separate model of the position of said positioning device and the obtained receive signal for each receiving element, said computing unit thereby more accurately determining position of said positioning device and therefor the target area during medical treatment of the target area, said computing unit estimating the position by a two stage search procedure,
  - a first stage comprising trying a number of equally spaced positions in the measurement range to establish a starting point in the model for each receiving element, and
  - a second stage comprising minimizing a difference between a vector corresponding to the measured receive signals and a calculated vector corresponding to the starting point using an iterative search process.

14. The system according to claim 13, wherein said system further comprising at least one reference transmitter connected to said control unit, each reference transmitter is configured to transmit a reference transmit signal, and a reference receive signal is measured at each receiving element, the control unit receives the measured receive signal from each receiving element, and the computing unit is configured to weight the measured receive signals to coincide with a reference model obtained according to claim 10, to obtain an automatic adjustment of the receiving elements during operation.

15. The system according to claim 13, wherein said at least one transmitter transmits a signal having a frequency within the range of 1 kHz-350 MHz and an amplitude difference from the transmitted signal is detected by the receiver at three, or more, positions to track variations of the transmitter.

* * * * *